US012582358B2

(12) United States Patent
Yin et al.

(10) Patent No.: US 12,582,358 B2
(45) Date of Patent: *Mar. 24, 2026

(54) SYSTEM AND METHOD FOR WEARABLE MEDICAL SENSOR AND NEURAL NETWORK BASED DIABETES ANALYSIS

(71) Applicant: The Trustees of Princeton University, Princeton, NJ (US)

(72) Inventors: Hongxu Yin, Princeton, NJ (US); Bilal Mukadam, Plano, TX (US); Xiaoliang Dai, Princeton, NJ (US); Niraj K. Jha, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 1008 days.

This patent is subject to a terminal disclaimer.

(21) Appl. No.: 17/619,449

(22) PCT Filed: Jun. 16, 2020

(86) PCT No.: PCT/US2020/037876
§ 371 (c)(1),
(2) Date: Dec. 15, 2021

(87) PCT Pub. No.: WO2020/257158
PCT Pub. Date: Dec. 24, 2020

(65) Prior Publication Data
US 2022/0240864 A1     Aug. 4, 2022

Related U.S. Application Data

(60) Provisional application No. 62/862,354, filed on Jun. 17, 2019.

(51) Int. Cl.
*A61B 5/00* (2006.01)
*A61B 5/0205* (2006.01)
(Continued)

(52) U.S. Cl.
CPC ........ *A61B 5/7264* (2013.01); *A61B 5/02055* (2013.01); *A61B 5/681* (2013.01);
(Continued)

(58) Field of Classification Search
None
See application file for complete search history.

(56) References Cited

U.S. PATENT DOCUMENTS 6,269,353 B1 * 7/2001 Sethi ........................ G06N 3/02
706/20
7,343,197 B2 * 3/2008 Shusterman ........... A61B 5/357
600/509
(Continued)

FOREIGN PATENT DOCUMENTS

WO 2018128927 A1 7/2018
WO 2019089339 A1 5/2019

OTHER PUBLICATIONS

Facchinetti, "Continuous glucose monitoring sensors: Past, present and future algorithmic challenges", Sensors, vol. 16, No. 12, pp. 2093-2104, 2016.

(Continued)

*Primary Examiner* — Maikhanh Nguyen
(74) *Attorney, Agent, or Firm* — Meagher Emanuel Laks Goldberg & Liao, LLP

(57) ABSTRACT

According to various embodiments, a machine-learning based system for diabetes analysis is disclosed. The system includes one or more processors configured to interact with a plurality of wearable medical sensors (WMSs). The processors are configured to receive physiological data from the WMSs and demographic data from a user interface. The processors are further configured to train at least one neural network based on a grow-and-prune paradigm to generate at least one diabetes inference model. The neural network grows at least one of connections and neurons based on (Continued)

gradient information and prunes away at least one of connections and neurons based on magnitude information. The processors are also configured to output a diabetes-based decision by inputting the received physiological data and demographic data into the generated diabetes inference model.

14 Claims, 12 Drawing Sheets

(51) Int. Cl.
    *G06N 3/045*        (2023.01)
    *G06N 3/082*        (2023.01)
(52) U.S. Cl.
    CPC ........... *A61B 5/7271* (2013.01); *G06N 3/045*
                (2023.01); *G06N 3/082* (2013.01)

(56) References Cited

U.S. PATENT DOCUMENTS

| | | | | |
|---|---|---|---|---|
| 10,806,404 | B2 * | 10/2020 | Soto ..................... | A61B 5/7275 |
| 11,426,102 | B2 * | 8/2022 | Frank ................... | A61B 5/7282 |
| 2004/0193064 | A1 | 9/2004 | Shusterman | |
| 2009/0012716 | A1 * | 1/2009 | Urdea .................... | G16H 50/30 |
| | | | | 435/6.12 |
| 2010/0234184 | A1 * | 9/2010 | Le Page ................ | A61B 5/1118 |
| | | | | 482/8 |
| 2014/0089232 | A1 * | 3/2014 | Buibas .................... | G06N 3/10 |
| | | | | 706/11 |
| 2015/0196801 | A1 * | 7/2015 | Erkkila .............. | A63B 24/0062 |
| | | | | 700/91 |
| 2016/0354039 | A1 * | 12/2016 | Soto ......................... | A61B 5/74 |
| 2021/0133540 | A1 * | 5/2021 | Dai ........................ | G06N 3/063 |

OTHER PUBLICATIONS

Yin et al., "A health decision support system for disease diagnosis based on wearable medical sensors and machine earning ensembles", IEEE Trans. Multi-Scale Computing Systems, vol. 3, No. 4, pp. 228-241, Oct.-Dec. 2017.

Zhang et al., "Transfer learning on fMRI datasets", Proc. Int. Conf., Artificial Intelligence and Statistics, 2018.

Yin et al., "Smart healthcare," Foundations and Trends in Electronic Design Automation, vol. 12, No. 4, pp. 401-466, 2018.

Quan et al., "Coding algorithms for defining comorbidities in ICD-9-CM and ICD-10 administrative data", Medical Care, vol. 43, No. 11, pp. 1130-1139, 2005.

Dai et al., "NeST: A neural network synthesis tool based on a grow-and-prune paradigm", IEEE Trans. on Computers, 2019.

Zheng et al., "A machine learning-based framework to identify type 2 diabetes through electronic health records", Int. J. Medical Informatics, vol. 97, pp. 120-127, Jan. 2017.

Fong et al., "Evaluation of stream mining classifiers for real-time clinical decision support system: A case study of blood glucose prediction in diabetes therapy", BioMed Research Int., vol. 2013, pp. 1-16, 2013.

Gamji et al., "A fuzzy classification system based on ant colony optimization for diabetes disease diagnosis," Expert Systems with Applications, vol. 38, No. 12, pp. 14650-14659, 2011.

Kavakiotis et al., "Machine learning and data mining methods in diabetes research," J. Computational and Structural Biotechnology, vol. 15, pp. 104-116, 2017.

Gulsham et al., "Development and validation of a deep learning algorithm for detection of diabetic retinopathy in retinal fundus photographs," J. American Medical Association, vol. 316, No. 22, pp. 2402-2410, Dec. 13, 2016.

Gargeya et al., "Automatedentification of diabetic retinopathy using deep learning," Ophthalmology, vol. 124, No. 7, pp. 962-969, Jul. 2017.

Ajjan et al., "Continuous glucose monitoring: A brief review for primary care practitioners", Advances in Therapy, vol. 36, No. 3, pp. 579-596, 2019.

Ballinger et al., "DeepHeart: Semi-supervised sequence learning for cardiovascular risk prediction", Proc. AAAI Conf., Artificial Intelligence, pp. 2079-2086, 2018.

Swapna et al., "Automated detection of diabetes using CNN and CNN-LSTM network and heart rate signals", Procedia Computer Science, vol. 132, pp. 1253-1262, 2018.

Sandler et al., "Inverted residuals and linear bottlenecks: Mobile networks for classification, detection and segmentation", arXiv preprint arXiv:1801.04381, 2018.

Ma et al., "ShuffleNet V2: Practical guidelines for efficient CNN architecture design", arXiv preprint arXiv:1807.11164, 2018.

Wu et al., "Shift: A zero FLOP, zeroparameter alternative to spatial convolutions", Proc. IEEE Conf. Computer Vision and Pattern Recognition, pp. 9127-9135, 2018.

Wu et al., "FBNet: Hardware-aware efficient ConvNet design via differentiable neural architecture search", Proc. IEEE Conf. Computer Vision and Pattern Recognition, 2019.

Zhou et al., "Neural architect: A multi-objective neural architecture search with performance prediction" , Proc. Conf. SysML, 2018.

Stamoulis et al., "Single-path NAS: Device-aware efficient ConvNet design", arXiv preprint arXiv: 1905.04159, 2019.

Dai et al., "ChamNet: Towards efficient network design through platform- aware model adaptation", Proc. IEEE Conf. Computer Vision and Pattern Recognition, 2019.

Han et al., "Learning both weights and connections for efficient neural network", Proc. Advances in Neural Information Processing Systems, pp. 1135-1143, 2015.

Han et al., "ESE: Efficient speech recognition engine with sparse LSTM on FPGA", Proc. ACM/SIGDA Int. Symp. Field-Programmable Gate Arrays, pp. 75-84, 2017.

Wen et al., "Learning intrinsic sparse structures within long short-term memory," arXiv: 1709.05027, 2018.

Narang et al., "Exploring sparsity in recurrent neural networks", arXiv1704.05119, 2017.

Dai et al., "Incremental learning using a grow-and-prune paradigm with efficient neural networks", arXiv:1905.10952, 2019.

Hassantabar et al., "SCANN: Synthesis of compact and accurate neural networks", arXiv:1904.09090, 2021.

Dai et al., "Grow and prune compact, fast, and accurate LSTMs", arXiv:1805.11797, 2018.

Zhu et al., "Trained ternary quantization," arXiv:1612.01064, 2017.

Jia et al., "A microprocessor implemented in 65nm CMOS with configurable and bit-scalable accelerator for programmable in-memory computing", arXiv: 1811.04047, 2018.

Zou et al., "Predicting Diabetes Mellitus With Machine Learning Techniques", Frontier in Genetics, vol. 9, Atricle 515, pp. 1-10, Nov. 2018.

International Search Report and Written Opinion for corresponding PCT Application No. PCT/US2020/037876, dated Sep. 14, 2020.

* cited by examiner

---

Figure 5:
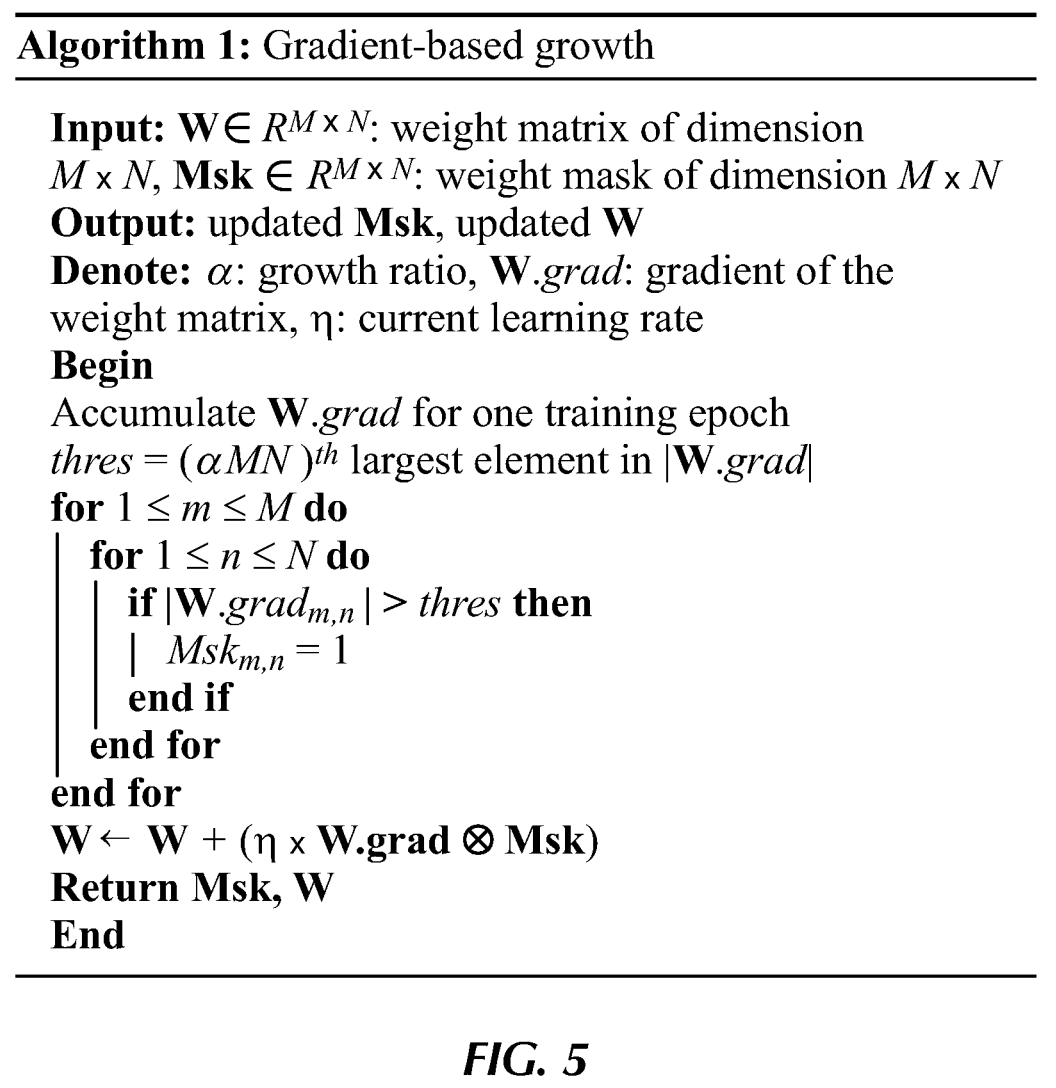

Algorithm 1: Gradient-based growth

---

Input: $\mathbf{W} \in R^{M \times N}$: weight matrix of dimension $M \times N$, Msk $\in R^{M \times N}$: weight mask of dimension $M \times N$
Output: updated Msk, updated W
Denote: $\alpha$: growth ratio, $\mathbf{W}.grad$: gradient of the weight matrix, $\eta$: current learning rate
Begin
Accumulate $\mathbf{W}.grad$ for one training epoch
$thres = (\alpha MN)^{th}$ largest element in $|\mathbf{W}.grad|$
for $1 \leq m \leq M$ do
$\quad$ for $1 \leq n \leq N$ do
$\quad\quad$ if $|\mathbf{W}.grad_{m,n}| > thres$ then
$\quad\quad\quad Msk_{m,n} = 1$
$\quad\quad$ end if
$\quad$ end for
end for
$\mathbf{W} \leftarrow \mathbf{W} + (\eta \times \mathbf{W}.grad \otimes \mathbf{Msk})$
Return Msk, W
End

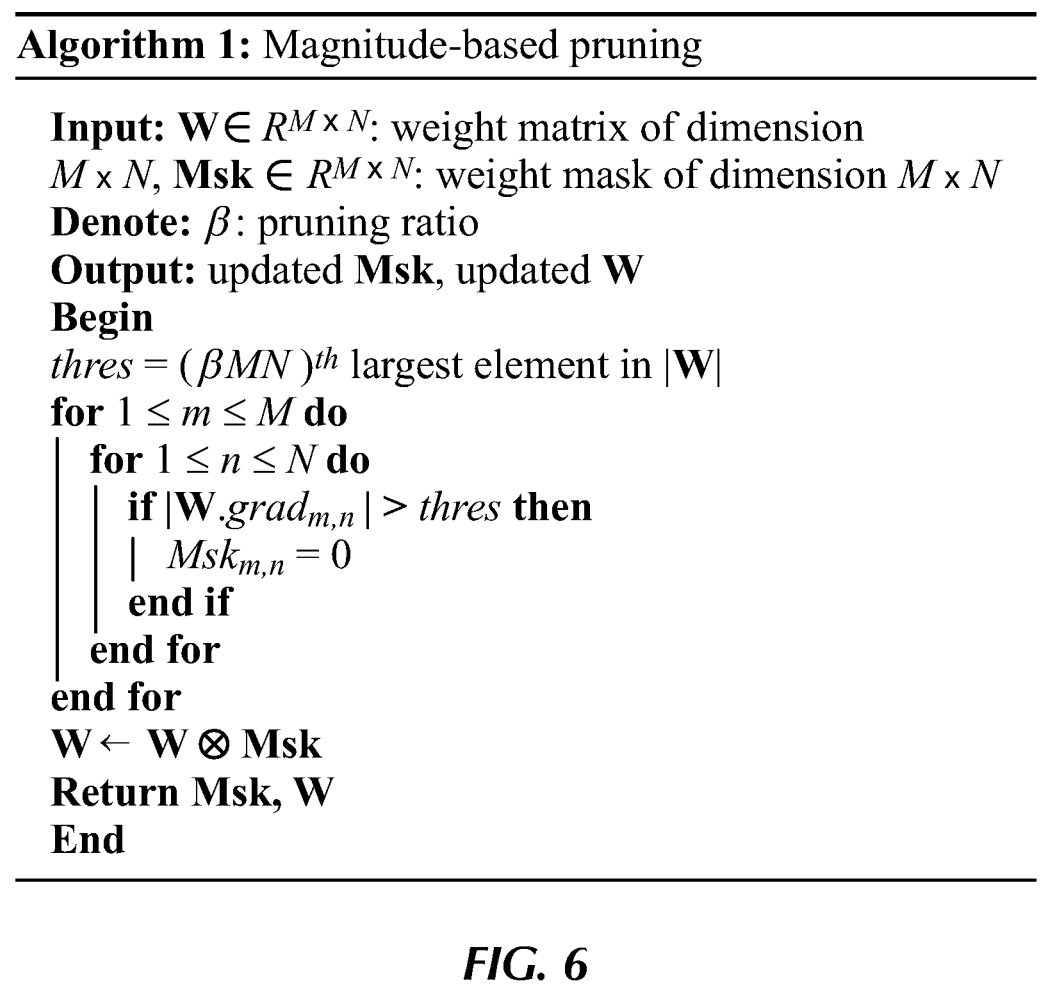

Algorithm 1: Magnitude-based pruning

Input: $\mathbf{W} \in R^{M \times N}$: weight matrix of dimension $M \times N$, $\mathbf{Msk} \in R^{M \times N}$: weight mask of dimension $M \times N$
Denote: $\beta$: pruning ratio
Output: updated $\mathbf{Msk}$, updated $\mathbf{W}$
Begin
*thres* $= (\beta MN)^{th}$ largest element in $|\mathbf{W}|$
for $1 \leq m \leq M$ do
  for $1 \leq n \leq N$ do
    if $|\mathbf{W}.grad_{m,n}| >$ *thres* then
      $Msk_{m,n} = 0$
    end if
  end for
end for
$\mathbf{W} \leftarrow \mathbf{W} \otimes \mathbf{Msk}$
Return Msk, W
End

*FIG. 6*

| Data Type | Source |
|---|---|
| Galvanic Skin Response | Smart Watch |
| Skin Temperature | Smart Watch |
| Acceleration (x,y,z) | Smart Watch |
| Inter-beat Interval | Smart Watch |
| Heart Rate | Smart Watch |
| Humidity | Smart Phone |
| Ambient Illuminance | Smart Phone |
| Ambient Light Color Spectrum | Smart Phone |
| Ambient Temperature | Smart Phone |
| Gravity (x,y,z) | Smart Phone |
| Angular Velocity (x,y,z) | Smart Phone |
| Orientation (x,y,z) | Smart Phone |
| Acceleration (x,y,z) | Smart Phone |
| Linear Acceleration (x,y,z) | Smart Phone |
| Air Pressure | Smart Phone |
| Proximity | Smart Phone |
| Wi-Fi Radiation Strength | Smart Phone |
| Magnetic Field Strength | Smart Phone |
| Age | Questionnaire |
| Gender | Questionnaire |
| Height | Questionnaire |
| Weight | Questionnaire |
| Relatives with Diabetes | Questionnaire |
| Smoking | Questionnaire |
| Drinking | Questionnaire |

*FIG. 8*

Prediction

| Label | | Diabetic | Healthy | Total |
|---|---|---|---|---|
| | Diabetic | 329 | 11 | 340 |
| | Healthy | 17 | 469 | 486 |
| | Total | 346 | 480 | 826 |

*FIG. 9*

Prediction

| Label | | Type-1 | Type-2 | Healthy | Total |
|---|---|---|---|---|---|
| | Type-1 | 275 | 0 | 7 | 282 |
| | Type-2 | 0 | 54 | 4 | 58 |
| | Healthy | 19 | 1 | 466 | 486 |
| | Total | 294 | 55 | 477 | 826 |

*FIG. 10*

Prediction

|  | Diabetic | Healthy | Total |
|---|---|---|---|
| Diabetic | 318 | 22 | 340 |
| Healthy | 15 | 471 | 486 |
| Total | 333 | 493 | 826 |

*Label* (row axis)

*FIG. 11*

Prediction

|  | Type-1 | Type-2 | Healthy | Total |
|---|---|---|---|---|
| Type-1 | 260 | 4 | 18 | 282 |
| Type-2 | 2 | 56 | 0 | 58 |
| Healthy | 14 | 1 | 471 | 486 |
| Total | 276 | 61 | 489 | 826 |

*Label* (row axis)

*FIG. 12*

| Performance Matrices | DiabNN-server | DiabNN-edge |
|---|---|---|
| Accuracy | 96.6% | 95.5% |
| FPR | 3.5% | 3.2% |
| FNR | 3.2% | 6.5% |
| FLOPs | 840.2K | 371.6K |
| #Parameters | 420.1K | 3.1K |

*FIG. 13*

| Model | Accuracy | #Parameters | Feature Extraction FLOPs | Classification FLOPs | Total FLOPs |
|---|---|---|---|---|---|
| SVM-linear | 86.9% | 375K | 0.49M | 0.75M | 1.24M |
| SVM-RBF | 92.6% | 653K | 0.49M | 1.31M | 1.79M |
| k-NN | 95.4% | 1.2M | 0.49M | 2.5M | 2.99M |
| Random Forest | 92.1% | 8K | 0.49M | 4K+ | 0.49M* |
| Linear Ridge | 81.3% | 0.8K | 0.49M | 1.6K | 0.49M |
| DiabNN-server | 96.6% | 420K | - | 0.84M | 0.84M |
| DiabNN-edge | 95.5% | 3.1K | - | 0.37M | 0.37M |

+: The number of comparison operations.
*: Calculation excluding the comparison operation cost.

*FIG. 14*

| | Data Sources | Model | Accuracy |
|---|---|---|---|
| Swapna et al. | ECG Sensor | Conv-LSTM | 95.1% |
| Swapna et al. | ECG Sensor | CNN | 93.6% |
| Ballinger et al. | Watch + Demographics | LSTM | 84.5% |
| Yin et al. | Watch + Demographics | Ensemble | 77.6% |
| This work (DiabNN-server) | Watch + Phone + Demographics | Stacked SC Layers | 96.6% |
| This work (DiabNN-edge) | Watch + Phone + Demographics | H-LSTM SR Layer | 95.5% |

*FIG. 15*

SYSTEM AND METHOD FOR WEARABLE MEDICAL SENSOR AND NEURAL NETWORK BASED DIABETES ANALYSIS

CROSS-REFERENCE TO RELATED APPLICATIONS

This application claims priority to provisional applications 62/862,354, filed Jun. 17, 2019, which is herein incorporated by reference in its entirety.

STATEMENT REGARDING FEDERALLY SPONSORED RESEARCH OR DEVELOPMENT

This invention was made with government support under Grant No. CNS-1617640 awarded by the National Science Foundation. The government has certain rights in the invention.

FIELD OF THE INVENTION

The present invention relates generally to wearable medical sensors and neural networks and, more particularly, to a system and method for diagnosis and monitoring of diabetes based on wearable medical sensor data and neural network processing that bypasses feature extraction.

BACKGROUND OF THE INVENTION

More than 422 million people around the world (more than 24 million in the U.S. alone) suffer from diabetes. This chronic disease imposes a substantial economic burden on both the patient and the government, and accounts for nearly 25% of the entire healthcare expenditure in the U.S. However, diabetes prevention, care, and especially early diagnosis are still fairly challenging given that the disease usually develops and gets treated outside a clinic, hence out of reach of advanced clinical care. It is estimated that more than 75% of the patients still remain undiagnosed. This may lead to irreversible and costly consequences. For example, studies have shown that the longer a person lives with undiagnosed and untreated diabetes, the worse their health outcomes are likely to be. Without an early alarm, people with pre-diabetes, a less intensive diabetes status that can be cured, could end up with diabetes mellitus within five years that can no longer be cured. Thus, it is urgent to develop an accessible and accurate diabetes diagnosis system for the daily life scenario, which can greatly improve general welfare and bend the associated healthcare expenditure downwards.

The emergence of wearable medical sensors (WMSs) points to a promising way to address this challenge. In the past decade, advancements in low-power sensors and signal processing techniques have led to many disruptive WMSs. These WMSs enable a continuous sensing of physiological signals during daily activities, and thus provide a powerful, yet user-transparent, human-machine interface for tracking the user's health status. Combining WMSs and machine learning brings up the possibility of pervasive health condition tracking and disease diagnosis in a daily context. This approach exploits the superior knowledge distillation capability of machine learning to extract medical insights from health-related physiological signals. Hence, it offers a promising method to bridge the information gap that currently separates the clinical and daily domains. This helps enable a unified smart healthcare system that serves people in both the daily and clinical scenarios.

However, disease diagnosis based on WMS data and its effective deployment at the edge still remain challenging. Conventional approaches typically involve feature extraction, model training, and model deployment. However, such an approach suffers from two major problems:

Inefficient feature extraction: Handcrafting features may require substantial engineering effort and expert domain knowledge for each targeted disease. Searching for informative features through trial-and-error can be very inefficient; hence, it may not be easy to effectively explore the available feature space. This problem is exacerbated when the feature space scales up given (i) a growing number of available signal types from WMSs, and (ii) more than 69,000 human diseases that need to be monitored.

Vast computation cost: Due to the presence of a vast amount of floating-point operations (FLOPs) involved in feature extraction and model inference, continuous health monitoring can be very computationally intensive, hence hard to deploy on resource-constrained platforms.

As such, there is a need for a disease analysis framework based on WMS data and machine learning that addresses at least the above deficiencies.

SUMMARY OF THE INVENTION

According to various embodiments, a machine-learning based system for diabetes analysis is disclosed. The system includes one or more processors configured to interact with a plurality of wearable medical sensors (WMSs). The processors are configured to receive physiological data from the WMSs and demographic data from a user interface. The processors are further configured to train at least one neural network based on a grow-and-prune paradigm to generate at least one diabetes inference model. The neural network grows at least one of connections and neurons based on gradient information and prunes away at least one of connections and neurons based on magnitude information. The processors are also configured to output a diabetes-based decision by inputting the received physiological data and demographic data into the generated diabetes inference model.

According to various embodiments, a machine-learning based method for diabetes analysis based on one or more processors configured to interact with a plurality of wearable medical sensors (WMSs) is disclosed. The method includes receiving physiological data from the WMSs and demographic data from a user interface. The method further includes training at least one neural network based on a grow-and-prune paradigm to generate at least one diabetes inference model. The neural network grows at least one of connections and neurons based on gradient information and prunes away at least one of connections and neurons based on magnitude information. The method also includes outputting a diabetes-based decision by inputting the received physiological data and demographic data into the generated diabetes inference model.

According to various embodiments, a non-transitory computer-readable medium having stored thereon a computer program for execution by a processor configured to perform a machine-learning based method for diabetes analysis is disclosed. The method includes receiving physiological data from one or more wearable medical sensors (WMSs) and demographic data from a user interface. The method further includes training at least one neural network based on a grow-and-prune paradigm to generate at least one diabetes inference model. The neural network grows at least one of connections and neurons based on gradient information and prunes away at least one of connections and neurons based on magnitude information. The method also includes outputting a diabetes-based decision by inputting the received physiological data and demographic data into the generated diabetes inference model.

Various other features and advantages will be made apparent from the following detailed description and the drawings.

BRIEF DESCRIPTION OF THE DRAWINGS

In order for the advantages of the invention to be readily understood, a more particular description of the invention briefly described above will be rendered by reference to specific embodiments that are illustrated in the appended drawings. Understanding that these drawings depict only exemplary embodiments of the invention and are not, therefore, to be considered to be limiting its scope, the invention will be described and explained with additional specificity and detail through the use of the accompanying drawings, in which:

FIG. 5 depicts a gradient based growth methodology according to an embodiment of the present invention;

FIG. 6 depicts a magnitude based pruning methodology according to an embodiment of the present invention;

FIG. 8 depicts a table of data types collected from each participant according to an embodiment of the present invention;

FIG. 9 depicts a table of a DiabNN-server confusion matrix for binary classification according to an embodiment of the present invention;

FIG. 10 depicts a table of a DiabNN-server confusion matrix for three-class classification according to an embodiment of the present invention;

FIG. 11 depicts a table of a DiabNN-edge confusion matrix for binary classification according to an embodiment of the present invention;

FIG. 12 depicts a table of a DiabNN-edge confusion matrix for three-class classification according to an embodiment of the present invention;

FIG. 13 depicts a table of performance comparison between DiabNN-server and DiabNN-edge according to an embodiment of the present invention;

FIG. 14 depicts a table of inference model comparison between DiabNNs and conventional frameworks according to an embodiment of the present invention; and FIG. 15 depicts a table of performance comparison between DiabDeep and prior work according to an embodiment of the present invention.

DETAILED DESCRIPTION OF THE INVENTION

Diabetes impacts the quality of life of millions of people around the globe. However, diabetes diagnosis is still an arduous but urgent process, given that this disease develops and gets treated outside the clinic. The emergence of wearable medical sensors (WMSs) and machine learning points to a potential way forward to address this challenge. WMSs enable a continuous yet user-transparent mechanism to collect and analyze physiological signals. However, disease diagnosis based on WMS data and its effective deployment on resource-constrained edge devices remain challenging due to inefficient feature extraction and vast computation cost.

To address these problems, generally disclosed herein are embodiments for a framework (referred to herein as DiabDeep) that combines efficient neural networks (called DiabNNs) with off-the-shelf WMSs for pervasive diabetes diagnosis. DiabDeep bypasses the feature extraction stage and acts directly on WMS data. It enables both an (i) accurate inference on the server, e.g., a desktop, and (ii) efficient inference on an edge device, e.g., a smartphone, to obtain a balance between accuracy and efficiency based on varying resource budgets and design goals. On the resource-fertile server, sparsely connected layers are stacked to deliver high accuracy. On the resource-scarce edge device, a hidden-layer LSTM based recurrent layer is used to substantially cut down on computation and storage costs while incurring only a minor accuracy loss. At the core of the framework lies a grow-and-prune training flow: it leverages gradient-based growth and magnitude-based pruning methodologies to enable DiabNNs to learn both weights and connections, while improving accuracy and efficiency.

The effectiveness of DiabDeep is demonstrated through a detailed analysis of data collected from 39 participants. For server (edge) side inference, a 96.6% (95.5%) accuracy is achieved in classifying diabetics against healthy individuals, and a 96.2% (95.3%) accuracy is achieved in distinguishing among type-1 diabetic, type-2 diabetic, and healthy individuals. Against conventional baselines, such as support vector machines with linear and radial basis function kernels, k-nearest neighbor, random forest, and linear ridge classifiers, DiabNNs achieve higher accuracy, while reducing the model size (floating-point operations) by up to 387.1×(8.1×). DiabDeep also cuts down on computation costs relative to conventional approaches. Therefore, the framework can be viewed as pervasive and efficient, yet very accurate.

System Overview

Figure 1:
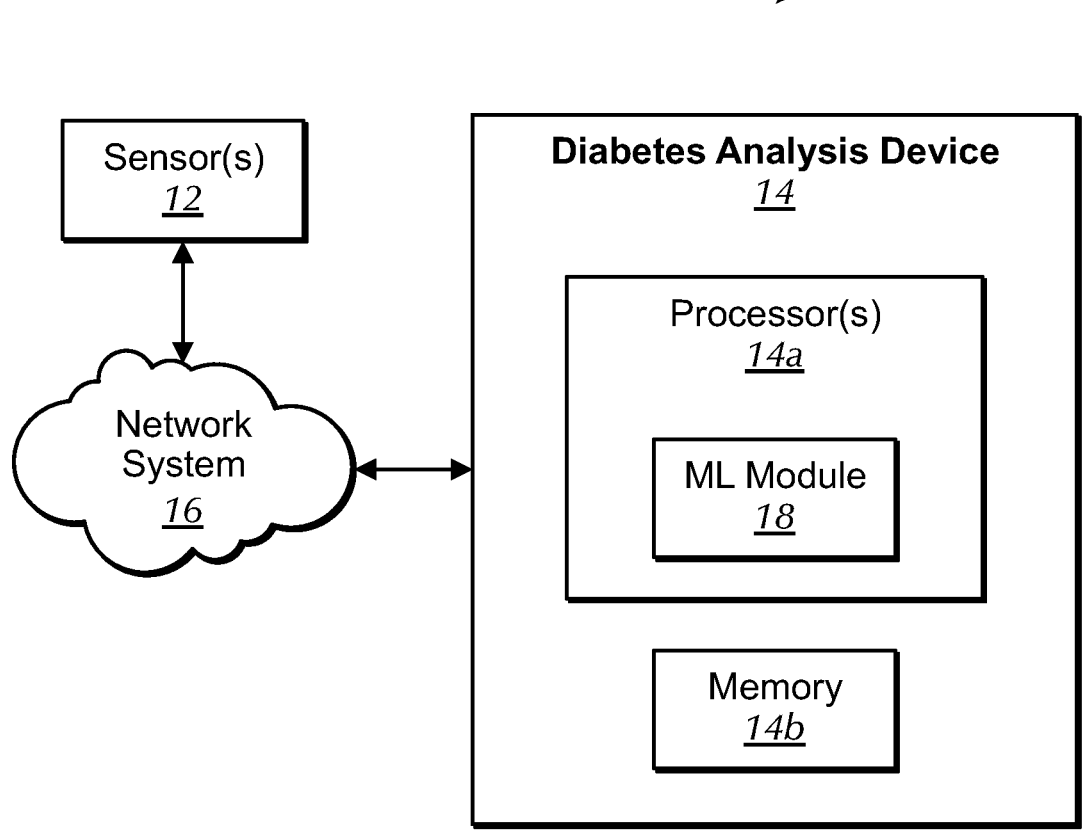
FIG. 1 depicts a block diagram of a system for implementing a DiabDeep framework according to an embodiment of the present invention.

FIG. 1 depicts a system 10 configured to implement machine learning based diabetes analysis from WMS data. The system 10 includes one or more wearable medical sensors (WMSs) 12. The WMSs 12 may be connected to a diabetes analysis device 14 via a network system 16. The WMSs 12 may also be integrated into the device 14, in which case a network system 16 is not required. The device 14 may be implemented in a variety of configurations including general computing devices such as but not limited to desktop computers, laptop computers, tablets, network appliances, and the like. The device 14 may also be implemented as a mobile device such as but not limited to a mobile phone, smart phone, smart watch, or tablet computer. Where the WMSs 12 are integrated into the device 14, the device 14 may be implemented as one or more IoT sensors.

The device 14 includes one or more processors 14*a* such as but not limited to a central processing unit (CPU), a graphics processing unit (GPU), or a field programmable gate array (FPGA) for performing specific functions and memory 14*b* for storing those functions. The processor 14*a* includes a machine learning (ML) module 18 for monitoring and diagnosing diabetes. The ML module 18 methodology will be described in greater detail below. It is also to be noted the training process for the ML module 18 may be implemented in a number of configurations with a variety of processors (including but not limited to central processing units (CPUs), graphics processing units (GPUs), and field programmable gate arrays (FPGAs)), such as servers, desktop computers, laptop computers, tablets, and the like.

The network system 16 may be implemented as a single network or a combination of multiple networks. Network system 16 may include but is not limited to wireless telecommunications networks, WiFi, Bluetooth, Zigbee, or other communications networks. Network system 16 may be a wired network as well.

Machine Learning for Diabetes Diagnosis

A number of studies have focused on applying machine learning to diabetes diagnosis from the clinical domain to the daily scenario.

Clinical approach: Electronic health records have been used as an information source for diabetes prediction and intervention. With the recent upsurge in the availability of biomedical datasets, new information sources have been unveiled for diabetes diagnosis, including gene sequences and retinal images. However, these approaches are still restricted to the clinical domain, hence have very limited access to patient status when he/she leaves the clinic.

Daily approach: Daily glucose level detection has recently captured an increasing amount of research attention. One stream of study has explored subcutaneous glucose monitoring for continuous glucose tracking in a daily scenario. However, this is an invasive approach that still requires a high level of compliance, relies on regular sensor replacement (3-14 days), and impacts user experience. Recent systems have started exploiting non-invasive WMSs to alleviate these shortcomings. For example, one system combined machine learning ensembles and non-invasive WMSs to achieve a diabetes diagnostic accuracy of 77.6%. Another system called DeepHeart that acts on Apple watch data and patient demographics uses bidirectional LSTMs to deliver an 84.5% diagnostic accuracy. However, it relies on a small spectrum of WMS signals that include only discrete heart rate and step count measurements (indirectly estimated by accelerometers and photoplethysmography). This may lead to information loss, hence reduce diagnostic capability. A third system achieved a 93.6% diagnostic accuracy by combining convolutional neural networks (CNNs) with LSTMs and heart rate variability measurements. However, this system has to rely on an electroencephalogram (ECG) data stream sampled at 500 Hz that is not yet well supported by commercial WMSs.

Efficient Neural Networks

Two NN configurations are approached next.

Compact model architecture: One stream of research exploits the design of efficient building blocks for NN redundancy removal. For example, MobileNetV2 stacks inverted residual building blocks to effectively shrink its model size and reduce its FLOPs. Another uses channel shuffle operation and depth-wise convolution to deliver model compactness. A third proposes ShiftNet based on shiftbased modules, as opposed to spatial convolution layers, to achieve substantial computation and storage cost reduction. Similarly, automated compact architecture design also provides a promising solution. One configuration develops efficient performance predictors to speed up the search process for efficient NNs. Compared to MobileNetV2 on the ImageNet dataset, the generated ChamNets achieve up to 8.5% absolute top-1 accuracy improvement while reducing inference latency substantially.

Network compression: Compression techniques have emerged as another popular direction for NN redundancy removal. The pruning methodology was initially demonstrated to be effective on large CNNs by reducing the number of parameters in AlexNet by 9× and VGG by 13× for the well-known ImageNet dataset, without any accuracy loss. Follow-up works have also successfully shown its effectiveness on recurrent NNs such as the LSTM. Network growth is a complementary method to pruning that enables a sparser yet more accurate model before pruning starts. A grow-and-prune synthesis paradigm typically reduces the number of parameters in CNNs and LSTMs by another 2×, and increases the classification accuracy. It enables NN based inference even on Internet-of-Things (IoT) sensors. The model can be further compressed through low-bit quantization. For example, one configuration showed that a ternary representation of the weights instead of full-precision (32-bit) in ResNet-56 can significantly reduce memory cost while incurring only a minor accuracy loss. The quantized models offer additional speedup potential for current NN accelerators.

The DiabDeep Framework

Figure 2:
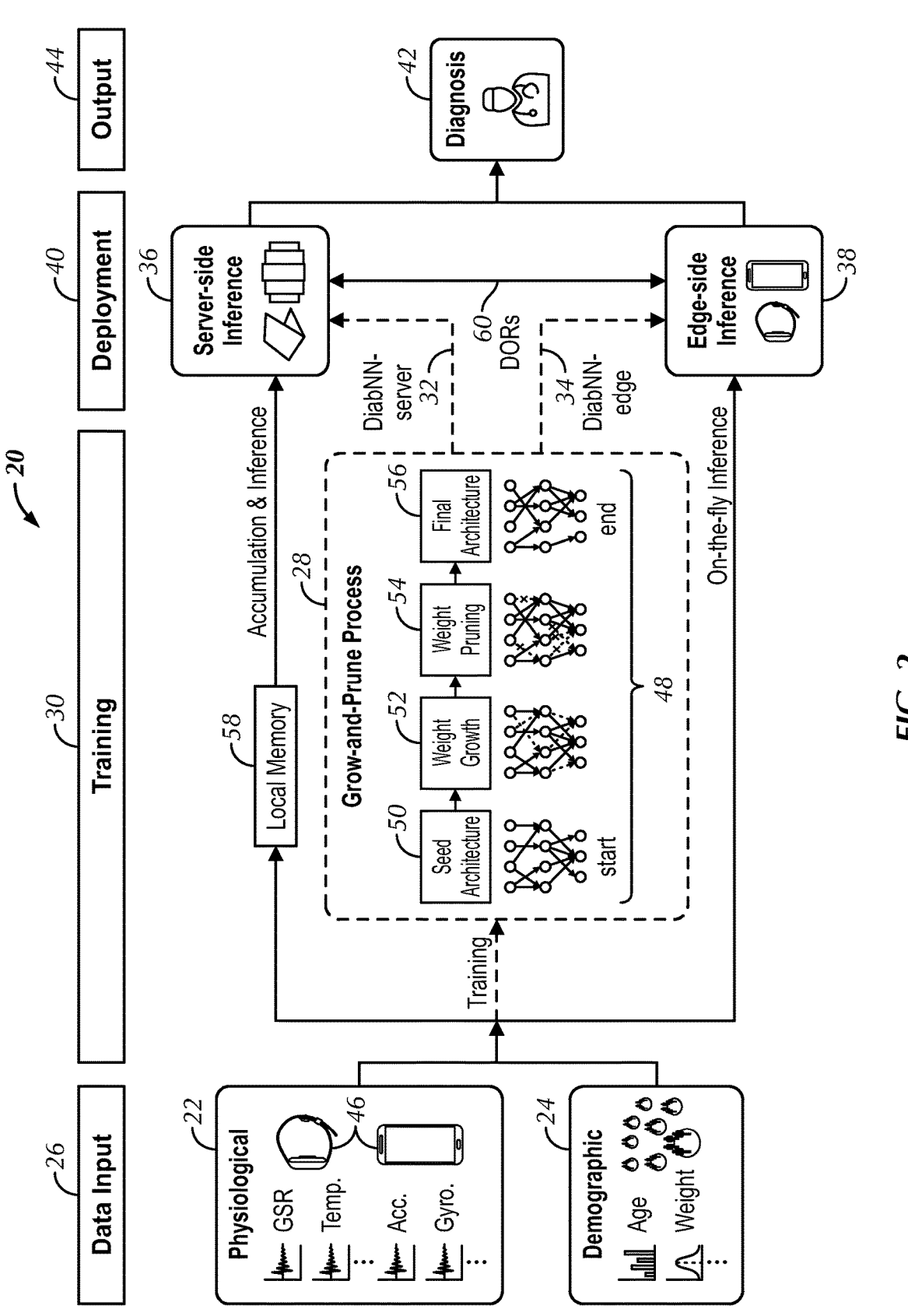
FIG. 2 depicts a schematic diagram of a DiabDeep framework according to an embodiment of the present invention.

The disclosed DiabDeep framework 20 is illustrated in FIG. 2. DiabDeep 20 captures both physiological 22 and demographic information 24 as data input 26. DiabDeep 20 deploys a grow-and-prune process training paradigm 28 for model training 30 to deliver two inference models, i.e., DiabNN-server 32 and DiabNN-edge 34, that enable inference on the server 36 and on the edge 38, respectively, in its deployment 40. Finally, DiabDeep 20 generates diagnosis 42 as output 44. The details of data input 26, model training 30, and model inference 40 are as follows.

Data input 26: As mentioned earlier, DiabDeep 20 focuses on (i) physiological signals 22 and (ii) demographic information 24 that are available in a daily context. Physiological signals 22 can be captured by WMSs 46 (e.g., smartphone and smartwatch) in a non-invasive, passive, and efficient manner. The list of collectible signals includes, but is not limited to, heart rate, body temperature, Galvanic skin response, and blood volume pulse. Additional signals such as electromechanical and ambient environmental data (e.g., accelerometer, gyroscope, and humidity sensor readings) may also provide information on user habit tracking that offers diagnostic insights. This list is expanding rapidly, given the speed of ongoing technological advancements in this field. Demographic information 24 (e.g., age, weight, gender, and height) also assists with disease diagnosis. It can be easily captured and updated through a simple user interface on a smartwatch or smartphone. Then, both physiological 22 and demographic data 24 are aggregated and merged into a comprehensive data input 26 for subsequent analysis.

Model training 30: DiabDeep 20 utilizes a grow-and-prune paradigm 28 to train its NNs 48 using the input data 26. It starts NN synthesis from a sparse seed architecture 50. It first allows the network 48 to grow connections and neurons based on gradient information 52. Then, it prunes away insignificant connections and neurons based on magnitude information 54 to drastically reduce model redundancy. This leads to a final architecture 56 with improved accuracy and efficiency, where the former is highly preferred on the server 36 and the latter is critical at the edge 38. The training process 30 generates two inference models, i.e., DiabNN-server 32 and DiabNN-edge 34, for server 36 and edge 38 inference, respectively. Both models share the same DiabNN architecture, but vary in the choice of internal NN layers based on different resource constraints and design objectives, to be explained later.

Model inference 40: Due to the distinct inference environments encountered upon deployment, DiabNNserver 32 and DiabNN-edge 34 require different input data flows, as depicted by the separate data paths in FIG. 2. In DiabNN-server 32, data have to be accumulated in local memory 58, e.g., local phone/watch storage, before they can be transferred to the base station 36 in a daily, weekly, or monthly manner, depending on user preference. As opposed to the accumulation-and-inference process, DiabNN-edge 34 enables on-the-fly inference directly at the edge 38, e.g., a smartphone. This enables users to receive instant diagnostic decisions 42 at output 44. As mentioned earlier, this incurs a slight accuracy degradation (around 1%) due to the scarce energy and memory budgets on the edge 38. However, this deficit may be alleviated when DiabNN-edge 34 jointly works with DiabNN-server 32. When an alarm is raised, DiabNN-edge 34 can store the relevant data sections as disease-onset records (DORs) 60 that can be later transferred to DiabNN-server 32 for further analysis. In this manner, DiabNN-edge 34 offers a substantial data storage reduction in the required edge memory by bypassing the storage of 'not-of-interest' signal sections, while preserving the capability to make accurate inference on the server side. Such DORs 60 can also be used as informative references if future physician intervention and checkup are needed.

Diagnosis Output 44: DiabDeep 20 generates diagnosis 42 as output 44 when DiabNN is fed the input data 26 from an individual.

The DiabNN Architecture

Figure 3:
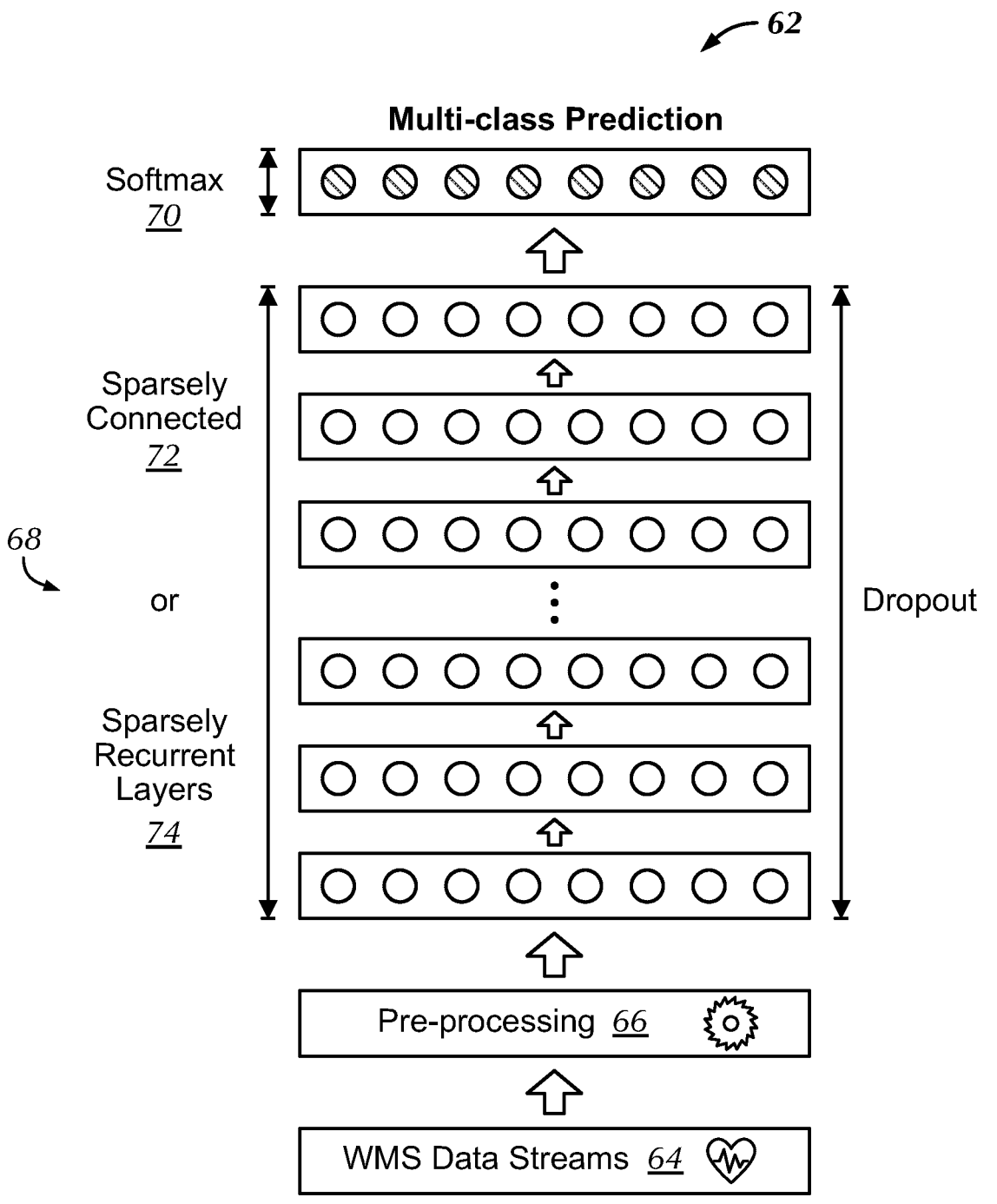
FIG. 3 depicts a schematic diagram of a DiabNN architecture according to an embodiment of the present invention.

FIG. 3 shows the DiabNN architecture 62 that distills diagnostic decisions from data inputs 64. There are three sequential steps employed during this process: (i) data preprocessing 66, (ii) transformation via NN layers 68, and (iii) output generation 70 (here using Softmax).

The preprocessing stage is critical for DiabNN 62 inference due to the following functionality.

Data normalization: NNs typically favor normalized inputs. Normalization methods, such as min-max scaling, standardization, and L2 normalization, generally lead to accuracy and noise tolerance improvements. In this embodiment, a min-max scaling is applied to scale each input data stream 64 into the [0,1] range:

$$x_{normalized} = \frac{x - \min(x)}{\max(x) - \min(x)} \tag{1}$$

Data alignment: WMS data streams 64 may vary in their start times and sampling frequencies. Therefore, data stream synchronization is guaranteed by checking their timestamps and applying appropriate offsets accordingly.

Different NN layers 68 are used in DiabNN 62 for server 32 and edge 34 inference. DiabNN-server 32 deploys sparsely connected (SC) layers 72 to aim at high accuracy whereas DiabNN-edge 34 utilizes sparsely recurrent (SR) layers 74 to aim at extreme efficiency. All NN layers 68 are subjected to dropout regularization, which is a widely-used approach for addressing overfitting and improving accuracy.

In DiabNN-server 32, each SC layer 72 conducts a linear transformation (using a sparse matrix as opposed to a full matrix) followed by a nonlinear activation function. As shown later, utilizing SC layers 72 leads to more model parameters than SR layers 74, hence leading to an improved learning capability and higher accuracy. Consequentially, DiabNN-server 32 achieves a 1.1% accuracy improvement over DiabNN-edge 34.

Figure 4:
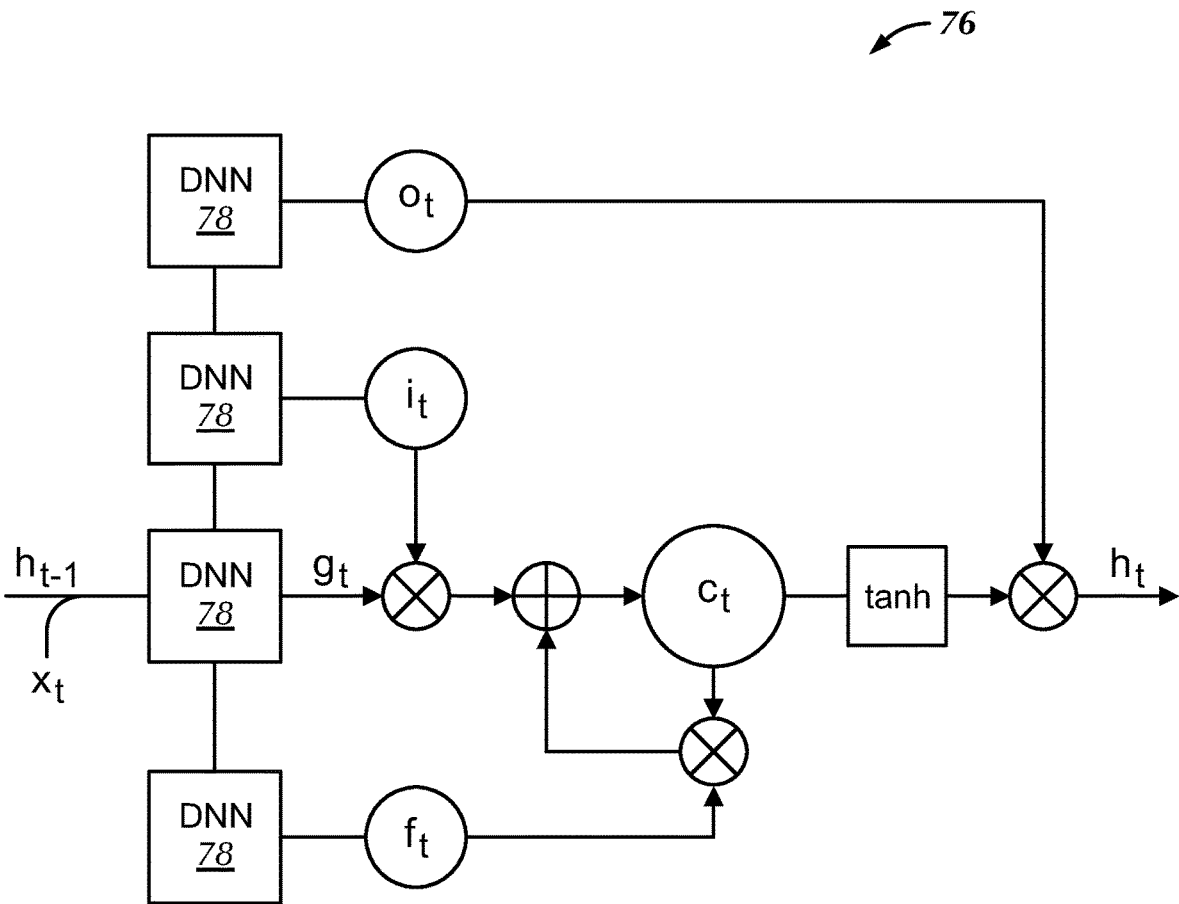
FIG. 4 depicts a schematic diagram of an H-LSTM cell according to an embodiment of the present invention.

In DiabNN-edge 34, the SR layer 74 design is based on an H-LSTM cell 76. It is a variant of an LSTM cell obtained through the addition of hidden layers to its control gates 78. FIG. 4 shows a schematic diagram of an H-LSTM 76. Its internal computation flow is governed by the following equations:

$$f_t = \sigma(W_f^s H^*([x_t, h_{t-1}]) + b_f) \tag{2}$$

$$i_t = \sigma(W_i^s H^*([x_t, h_{t-1}]) + b_o) \tag{3}$$

$$o_t = \sigma(W_o^s H^*([x_t, h_{t-1}]) + b_o) \tag{4}$$

$$g_t = \tanh(W_g^s H^*([x_t, h_{t-1}]) + b_g) \tag{5}$$

$$c_t = f_t \otimes c_{t-1} + i_t \otimes g_t \tag{6}$$

$$h_t = o_t \otimes \tanh(c_t) \tag{7}$$

Here, $f_t$, $i_t$, $o_t$, $g_t$, $x_t$, $h_t$, and $c_t$ denote the forget gate, input gate, output gate, cell update vector, input, hidden state, and cell state at step t, respectively. Further, $h_{t-1}$ and $c_{t-1}$ refer to the previous hidden and cell states at step t−1. Yet further, H, $W^s$, b, $\sigma$, and $\otimes$ refer to a hidden layer that performs a linear transformation followed by an activation function, sparse weight matrix, bias, sigmoid function, and element-wise multiplication, respectively. Yet further, * indicates zero or more H layers for each NN gate 78. The additional hidden layers enable three advantages. First, they enhance gate control through a multi-level hierarchy that can lead to accuracy gains. Second, they can be easily regularized through dropout, and thus lead to better generalization. Third, they offer a wide range of choices for internal activation functions, such as the rectified linear unit (ReLU) as a nonlimiting example, that can lead to faster learning. Using H-LSTM based SR layers 74, DiabNN-edge 34 reduces the model size by 135.5× and inference FLOPs by 2.3× relative to DiabNN-server 32.

Grow and Prune Training 28 for DiabNN 62

The gradient-based network growth and magnitude-based network pruning algorithms are next explained in detail. Unless otherwise stated, a mask-based approach is assumed for tackling sparse networks. Each weight matrix W has a corresponding binary mask matrix Msk that has the exact same size. It is used to disregard dormant connections (connections with zero-valued weights).

The methodology in FIG. 5 illustrates the connection growth process. The main objective of the weight growth phase is to locate only the most effective dormant connections to reduce the value of the loss function L. To do so, the gradient for all the dormant connections are first evaluated and this information is used as a metric for ranking their effectiveness. During the training process, the gradient of all weight matrices (W.grad) is extracted for each mini-batch of training data using the back-propagation algorithm. This process is repeated over a whole training epoch to accumulate W.grad. Then, the average gradient is calculated over the entire epoch by dividing the accumulated values by the number of training instances. A dormant connection w is activated if and only if its gradient magnitude is larger than the $((1-\alpha)\times100)^{th}$ percentile of the gradient magnitudes of its associated layer matrix. Its initial value is set to the product of its gradient value and the current learning rate. The growth ratio $\alpha$ is a hyperparameter where $0.1 \leq \alpha \leq 0.3$ is typically used here, though that is not intended to be limiting. The NN growth method has been shown to be very effective in enabling the network to reach a higher accuracy with far less redundancy than a fully connected model.

The connection pruning methodology is shown in FIG. 6. During this process, a connection w is removed if and only if its magnitude is smaller than the $(\beta \times 100)^{th}$ percentile of the weight magnitudes of its associated layer matrix. When pruned away, the connection's weight value and its corresponding mask binary value are simultaneously set to zero. The pruning ratio $\beta$ is also a hyperparameter where $\beta \leq 0.3$ is typically used here, though that is not intended to be limiting. Connection pruning is an iterative process, where the network is retrained to recover its accuracy after each pruning iteration.

Evaluating Performance of an Embodiment of DiabDeep

The DiabDeep framework is implemented here using PyTorch on Nvidia GeForce GTX 1060 GPU (with 1.708 GHz frequency and 6 GB memory) and Tesla P100 GPU (with 1.329 GHz frequency and 16 GB memory). CUDA 8.0 and CUDNN 5.1 libraries are employed in the following experiments. First the dataset collected from 39 participants that is used for DiabDeep evaluation is described. Then, the performance of DiabNN-server and DiabNN-edge is analyzed for two classification tasks: (i) binary classification that distinguishes between diabetic vs. healthy individuals, and (ii) three-class classification to distinguish among type-1 diabetic, type-2 diabetic, and healthy individuals.

Figure 7:
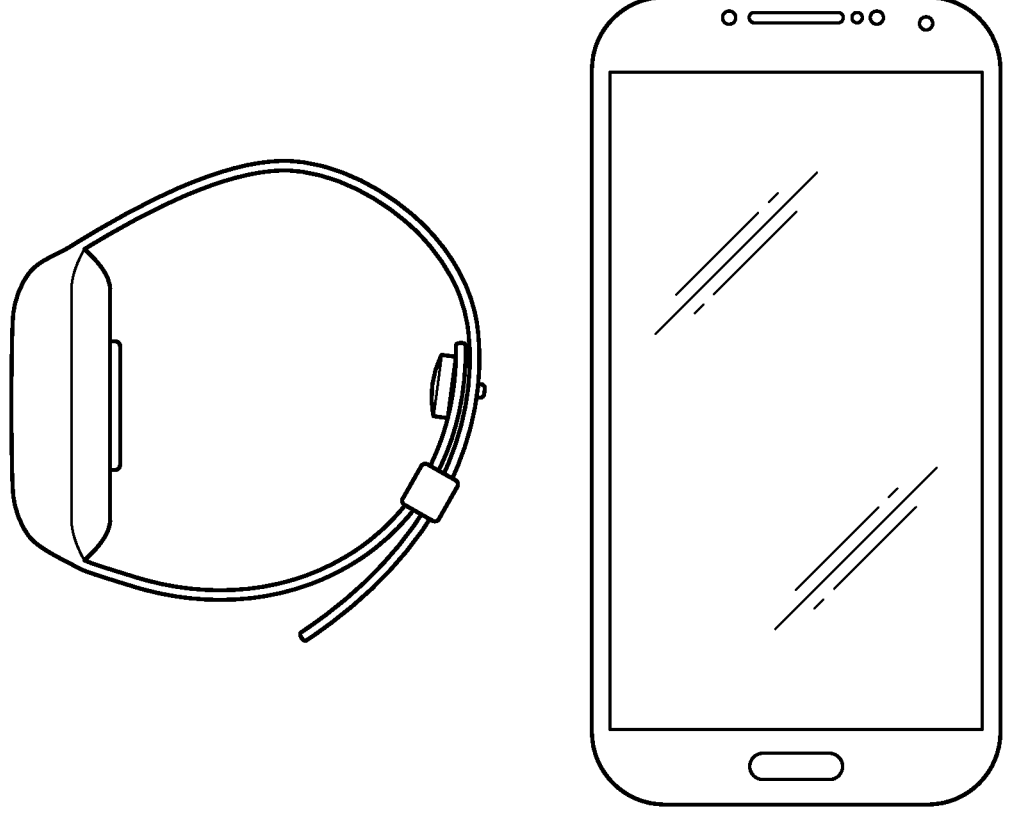
FIG. 7 depicts a photo of a smartwatch and smartphone used for data collection according to an embodiment of the present invention.

Data Collection and Preparation:

Here, the physiological data and demographic information from 39 participants was collected. 14 participants were diagnosed with diabetes (11 with type-1 and three with type-2 diabetes) whereas the remaining 25 participants were healthy non-diabetic baselines. The physiological data was collected using a commercially available Empatica E4 smartwatch and Samsung Galaxy S4 smartphone, as shown in FIG. 7. A questionnaire was also used to gather demographic information from all the participants. All the data types collected are summarized in the table in FIG. 8.

During data collection, all the participants are first informed about the experiment, are asked to sign a consent form, and are asked to fill the demographic questionnaire. Then, the Empatica E4 smartwatch is placed on the wrist of a participant's non-dominant hand, and the Samsung Galaxy S4 smartphone in the participant's pocket. The experiment lasts for approximately 1.5 hours in which the smartwatch and smartphone continuously track and store the physiological signals. The Empatica E4 Connect portal is used for smartwatch data retrieval. An Android application is developed to record all the smartphone sensor data streams. All the data streams contain detailed timestamps that are later used for data synchronization. The experimental procedure was approved by the Institutional Review Board of Princeton University. None of the participants reported mental, cardiac, or endocrine disorders.

The dataset is preprocessed before training the model. The WMS data streams are first synchronized and windowed. To avoid time correlation between adjacent data windows, the data is divided into t=15s windows with s=30s shifts in between. The final dataset contains 4130 data instances. 70%, 10%, and 20% of the data is used as training, validation, and test sets. The training, validation, and test sets have no time overlap. The value ranges of the data streams are then extracted from the training set, and then all three datasets are scaled based on the min-max scaling method, as explained earlier.

DiabNN-Server Performance Evaluation:

The detailed experimental results for DiabNN-server are first presented.

Data input: For each data instance, the data is flattened and concatenated within the same monitoring window from both the smartphone and smartwatch. This results in a vector of length 3705, where the flattened smartwatch window contains 2535 signal readings (from one data stream at 64 Hz, three data streams at 32 Hz, two data streams at 4 Hz, and one data stream at 1 Hz), and the flattened smartphone window provides additional 1170 signal readings (from 26 data streams at 3 Hz). Finally, the seven demographic features are appended at its end and a vector of length 3712 is obtained as the input for DiabNN-server.

Model architecture: Five sequential SC layers are used in DiabNN-server with widths set at 1024, 512, 256, 128, and 64, respectively. The input dimension is the same as the input tensor dimension of 3712. ReLU is used as the nonlinear activation function for all SC layers.

Training: A stochastic gradient descent (SGD) optimizer with a momentum of 0.9 is used for this experiment. The learning rate is initialized to 0.01 and the learning rate is divided by 10 when the validation accuracy does not increase in 50 consecutive epochs. A batch size of 256 and a dropout ratio of 0.2 is used. For grow-and-prune training, the seed architecture is initialized with a filling rate of 20%. The network is grown for three epochs using a 0.2 growth ratio. For network pruning, the pruning ratio is initialized to 0.2. The pruning ratio is halved if the retrained model cannot restore accuracy on the validation set. The process is terminated when the ratio falls below 0.01.

The table in FIG. 9 presents the confusion matrix of DiabNN-server for the binary classification task. DiabNN-server achieves an overall accuracy of 96.6%. For the healthy instances, it achieves a very low false positive rate (FPR), which is the ratio of the number of false predictions of disease onset (positive) over the total number of healthy instances (negative), of 3.5%, demonstrating its effectiveness in avoiding false alarms. For the diabetic instances, it achieves a false negative rate (FNR) of 3.2%, indicating its effectiveness in raising alarms when diabetes does occur.

The confusion matrix of DiabNN-server for the three-class classification task is presented in the table in FIG. 10. DiabNN-server achieves an overall accuracy of 96.2%. For the healthy instances, it achieves a low FPR of 4.1%, again demonstrating its ability to avoid false alarms. It also delivers low FNRs for both type-1 and type-2 diabetic individuals of 2.5% and 6.9%, respectively (each FNR depicts the ratio of the number of false predictions for a target diabetes type divided by the total number of instances of that type).

Furthermore, the grow-and-prune training paradigm not only delivers high diagnostic accuracy, but also leads to model compactness as a side benefit. For binary classification, the final DiabNN-server model contains only 420.1K parameters with a sparsity level of 90.7%. For the three-class classification task, the final DiabNN-server model contains only 441.3K parameters with a sparsity level of 90.2%. The model compactness achieved in both cases can help reduce storage and energy consumption on the server.

DiabNN-Edge Performance Evaluation:

The performance of DiabNN-edge is next analyzed.

Data input: Unlike SC layer based DiabNN-server, SR layer based DiabNN-edge acts on time series data step by step. Thus, at each time step, the temporal signal values are concatenated from each data stream along with the demographic information to form an input vector of length 40 (corresponding to seven smartwatch data streams, 26 smartphone data streams, and seven demographic features, as shown in FIG. 8). DiabNN-edge operates on four input vectors per second. When a signal reading is missing in a data stream (e.g., due to a lower sampling frequency), the closest previous reading is used in that data stream as the interpolated value.

Model architecture: DiabNN-edge contains one HLSTM cell based SR layer that has a hidden state width of 96. Each control gate within the H-LSTM cell contains one hidden layer. ReLU is used as the nonlinear activation function.

Training: An SGD optimizer is used with a momentum of 0.9 for this experiment. The learning rate is initialized to 0.001. The learning rate is divided by 10 when the validation accuracy does not increase in 30 consecutive epochs. A batch size of 64 and a dropout ratio of 0.2 is used for training. For grow-and-prune training, the same hyperparameter set as in the experiment for DiabNN-server is used.

The confusion matrix of DiabNN-edge for the binary classification task is presented in the table in FIG. 11. DiabNN-edge achieves an overall accuracy of 95.5%. For the healthy case, it also achieves a very low FPR of 3.1%. For diabetic instances, it achieves an FNR of 6.5%. This shows that DiabNN-edge can also effectively raise disease alarms on the edge.

DiabNN-edge for the three-class classification task is also evaluated and the confusion matrix is presented in the table in FIG. 12. DiabNN-edge achieves an overall accuracy of 95.3%. For the healthy case, it achieves an FPR of 3.1%. It achieves FNRs of 7.8% and 3.4% for the type-1 and type-2 diabetic instances, respectively.

DiabNN-edge delivers extreme model compactness. For binary classification, the final DiabNN-edge model contains a sparsity level of 96.5%, yielding a model with only 3.1K parameters. For the three-class classification task, the final DiabNN-edge model contains a sparsity level of 96.3%, yielding a model with only 3.3K parameters. This greatly assists with inference on the edge that typically suffers from very limited resource budgets.

Results:

As mentioned earlier, DiabNN-edge and DiabNN-server offer several performance trade-offs over diagnostic accuracy, storage cost, and run-time efficiency. This provides flexible design choices that can accommodate varying design objectives related to model deployment. To illustrate their differences, these two models are compared for the binary classification task in the table in FIG. 13. It is observed that DiabNN-server achieves a higher accuracy and a lower FNR. DiabNN-edge, on the other hand, caters to edge-side inference by enabling:

(1) A smaller model size: The edge model contains 135.5× fewer parameters, leading to a substantial memory reduction.

(2) Less computation: It requires 2.3× fewer FLOPs per inference, enabling a more efficient, hence more frequent, monitoring capability on the edge.

(3) A lower FPR: It reduces the FPR by 0.3%. This enables fewer false alarms and hence an improved usability for the system in a daily usage scenario.

Next, DiabNNs is compared with previously used learning methods, including SVMs with linear and RBF kernels, k-NN, random forest, and linear ridge classifiers. For all the methods, the same train/validation/test split and the same binary classification task are used for a fair comparison. In line with previous studies, the signal mean, variance, Fourier transform coefficients, and the third-order Daubechies wavelet transform approximation and detail coefficients on Daubechies D2, D4, D8, and D24 filters are extracted from each monitoring window, resulting in a feature vector of length 304 per data instance. All the not-NN baselines are trained using the Python-based Scikit learn libraries. The performance of all the inference models is compared in the table in FIG. 14. In addition to classification accuracy, the necessary FLOPs per inference involved in both feature extraction and classification stages are also computed. It can be seen that DiabNN-server achieves the highest accuracy among all the models. With a higher accuracy than all the not-NN baselines, DiabNN-edge achieves the smallest model size (up to 387.1× reduction) and least FLOPs per inference (up to 8.1× reduction). Note that the feature extraction stage accounts for 491K FLOPs even before the classification stage starts executing. This is already 1.3× the total inference cost of DiabNN-edge.

DiabDeep is compared with previous work in the table in FIG. 15. The same binary classification task that is the focus of these studies is also focused on. DiabDeep achieves the highest accuracy relative to the baselines due to its two major advantages. First, it relies on a more comprehensive set of WMSs. This captures a wider spectrum of user signals in the daily context for diagnostic decisions. Moreover, it utilizes a grow-and-prune training paradigm that learns both the connections and weights for DiabNNs. This enables a more effective SGD in both the model architecture space and parameter space.

Conclusion:

As such, generally disclosed herein are embodiments for a framework called DiabDeep that combines WMSs with efficient DiabNNs for continuous and pervasive diabetes diagnosis on both the server and the edge. On the resource-rich server, stacked SC layers are deployed to focus on high accuracy. On the resource-scarce edge, an H-LSTM based SR layer is used to reduce computation and storage costs with only a minor accuracy loss. DiabNNs are trained by leveraging gradient-based growth and magnitude-based pruning methodologies. This enables DiabNNs to learn both weights and connections during training. DiabDeep is evaluated based on data collected from 39 participants. Embodiments of the disclosed system achieve a 96.6% (95.5%) accuracy in classifying diabetics against healthy individuals on the server (edge), and a 96.2% (95.3%) accuracy in distinguishing among type-1 diabetic, type-2 diabetic, and healthy individuals. Against previous baselines, such as SVMs with linear and RBF kernels, k-NN, random forest, and linear ridge classifiers, DiabNN-edge reduces model size (FLOPs) by up to 387.1×(8.1×) while improving accuracy. Thus, it is demonstrated that DiabDeep can be employed in a pervasive fashion, while offering high efficiency and accuracy.

It is understood that the above-described embodiments are only illustrative of the application of the principles of the present invention. The present invention may be embodied in other specific forms without departing from its spirit or essential characteristics. All changes that come within the meaning and range of equivalency of the claims are to be embraced within their scope. Thus, while the present invention has been fully described above with particularity and detail in connection with what is presently deemed to be the most practical and preferred embodiment of the invention, it will be apparent to those of ordinary skill in the art that numerous modifications may be made without departing from the principles and concepts of the invention as set forth in the claims.

What is claimed is:

1. A machine-learning based system for diabetes analysis, comprising one or more processors configured to interact with a plurality of wearable medical sensors (WMSs), the processors configured to:

receive physiological data from the WMSs and demographic data from a user interface;

train at least one neural network based on a grow-and-prune paradigm to generate at least one diabetes inference model, the neural network to grow at least one of connections and neurons based on gradient information and to prune away at least one of connections and neurons based on magnitude information; and output a diabetes-based decision by inputting the received physiological data and demographic data into the generated diabetes inference model, wherein the growing at least one of connections and neurons based on gradient information comprises adding connection or neuron when its gradient magnitude is greater than a predefined percentile of gradient magnitudes based on a growth ratio, and wherein the pruning away at least one of connections and neurons based on magnitude information comprises removing a connection or neuron when its magnitude is less than a predefined percentile of magnitudes based on a pruning ratio.

2. The system of claim 1, wherein the physiological data comprises at least one of heart rate, body temperature, galvanic skin response, and blood volume pulse.

3. The system of claim 1, wherein the physiological data comprises electromechanical data and ambient environmental data.

4. The system of claim 1, wherein the demographic data comprises at least one of age, weight, gender, and height.

5. The system of claim 1, wherein the generated inference model comprises at least one of a server-based inference model and an edge-based inference model.

6. A machine-learning based method for diabetes analysis based on one or more processors configured to interact with a plurality of wearable medical sensors (WMSs), the method comprising:

receiving physiological data from the WMSs and demographic data from a user interface;

training at least one neural network based on a grow-and-prune paradigm to generate at least one diabetes inference model, the neural network to grow at least one of connections and neurons based on gradient information and to prune away at least one of connections and neurons based on magnitude information; and outputting a diabetes-based decision by inputting the received physiological data and demographic data into the generated diabetes inference model, wherein the growing at least one of connections and neurons based on gradient information comprises adding connection or neuron when its gradient magnitude is greater than a predefined percentile of gradient magnitudes based on a growth ratio, and wherein the pruning away at least one of connections and neurons based on magnitude information comprises removing a connection or neuron when its magnitude is less than a predefined percentile of magnitudes based on a pruning ratio.

7. The method of claim 6, wherein the physiological data comprises at least one of heart rate, body temperature, galvanic skin response, and blood volume pulse.

8. The method of claim 6, wherein the physiological data comprises electromechanical data and ambient environmental data.

9. The method of claim 6, wherein the demographic data comprises at least one of age, weight, gender, and height.

10. A non-transitory computer-readable medium having stored thereon a computer program for execution by a processor configured to perform a machine-learning based method for diabetes analysis, the method comprising:

receiving physiological data from one or more wearable medical sensors (WMSs) and demographic data from a user interface;

training at least one neural network based on a grow-and-prune paradigm to generate at least one diabetes inference model, the neural network to grow at least one of connections and neurons based on gradient information and to prune away at least one of connections and neurons based on magnitude information; and outputting a diabetes-based decision by inputting the received physiological data and demographic data into the generated diabetes inference model, wherein the growing at least one of connections and neurons based on gradient information comprises adding connection or neuron when its gradient magnitude is greater than a predefined percentile of gradient magnitudes based on a growth ratio, and wherein the pruning away at least one of connections and neurons based on magnitude information comprises removing a connection or neuron when its magnitude is less than a predefined percentile of magnitudes based on a pruning ratio.

11. The non-transitory computer-readable medium of claim 10, wherein the physiological data comprises at least one of heart rate, body temperature, galvanic skin response, and blood volume pulse.

12. The non-transitory computer-readable medium of claim 10, wherein the physiological data comprises electromechanical data and ambient environmental data.

13. The non-transitory computer-readable medium of claim 10, wherein the demographic data comprises at least one of age, weight, gender, and height.

14. The non-transitory computer-readable medium of claim 10, wherein the generated inference model comprises at least one of a server-based inference model and an edge-based inference model.

* * * * *